US006905672B2

(12) United States Patent
Rajaiah et al.

(10) Patent No.: US 6,905,672 B2
(45) Date of Patent: Jun. 14, 2005

(54) COMPOSITIONS AND METHODS TO INHIBIT TARTAR AND MICROBES USING DENTURE ADHESIVE COMPOSITIONS WITH COLORANTS

(75) Inventors: Jayanth Rajaiah, Loveland, OH (US); Kimberly Ann Gilday-Weber, Cincinnati, OH (US); Lisa Catron Ernst, Cincinnati, OH (US); Timothy Sadley Owens, Loveland, OH (US); John E. Barnes, Maineville, OH (US); Nivedita Ramji, Mason, OH (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

(21) Appl. No.: 10/218,632

(22) Filed: Aug. 14, 2002

(65) Prior Publication Data

US 2003/0108488 A1 Jun. 12, 2003

Related U.S. Application Data

(63) Continuation-in-part of application No. 09/716,766, filed on Nov. 20, 2000, now Pat. No. 6,475,497, which is a continuation-in-part of application No. 09/716,820, filed on Nov. 20, 2000, now Pat. No. 6,475,498, which is a continuation-in-part of application No. 09/716,810, filed on Nov. 20, 2000, now Pat. No. 6,677,391.
(60) Provisional application No. 60/169,703, filed on Dec. 8, 1999, provisional application No. 60/169,558, filed on Dec. 8, 1999, and provisional application No. 60/169,702, filed on Dec. 8, 1999.

(51) Int. Cl.$^7$ .................. A61K 7/16; A61C 13/225
(52) U.S. Cl. .................. 424/49; 424/52; 424/54; 433/180; 433/215; 433/216; 433/228.1
(58) Field of Search .................. 424/49, 52, 54; 433/180, 215, 216, 228.1; 523/120

(56) References Cited

U.S. PATENT DOCUMENTS

| 3,429,963 | A | | 2/1969 | Shedlovsky |
| 3,557,783 | A | | 1/1971 | Castner |
| 3,736,274 | A | | 5/1973 | Schoenholz et al. |
| 3,894,154 | A | | 7/1975 | Graff et al. |
| 3,941,772 | A | | 3/1976 | Ploger et al. |
| 3,955,281 | A | | 5/1976 | Weitzman |
| 3,956,480 | A | | 5/1976 | Dichter et al. |
| 3,960,888 | A | | 6/1976 | Ploger et al. |
| 3,988,443 | A | | 10/1976 | Ploger et al. |
| 4,138,477 | A | | 2/1979 | Gaffar |
| 4,138,814 | A | | 2/1979 | Weitzman |
| 4,315,779 | A | | 2/1982 | Heyd et al. |
| 4,316,915 | A | | 2/1982 | Friello et al. |
| 4,324,547 | A | | 4/1982 | Arcan et al. |
| 4,348,378 | A | * | 9/1982 | Kosti .................. 424/9.71 |
| 4,352,823 | A | | 10/1982 | Cherukuri et al. |
| 4,372,942 | A | | 2/1983 | Cimiluca |
| 4,466,983 | A | | 8/1984 | Cifrese et al. |
| 4,554,154 | A | | 11/1985 | White |
| 4,597,970 | A | | 7/1986 | Sharma et al. |
| 4,627,977 | A | | 12/1986 | Gaffar et al. |
| 4,642,235 | A | | 2/1987 | Reed et al. |
| 4,683,138 | A | | 7/1987 | Glass et al. |
| 4,728,291 | A | | 3/1988 | Golub |
| 4,741,941 | A | | 5/1988 | Englebert et al. |
| 4,786,253 | A | | 11/1988 | Morais |
| 4,799,888 | A | | 1/1989 | Golub |
| 4,808,418 | A | | 2/1989 | Zamudio-Tena et al. |
| 4,900,554 | A | | 2/1990 | Yanagibashi et al. |
| 4,908,211 | A | | 3/1990 | Paz |
| 4,975,288 | A | | 12/1990 | Hager et al. |
| 5,017,385 | A | | 5/1991 | Wienecke |
| 5,037,924 | A | | 8/1991 | Tazi et al. |

(Continued)

FOREIGN PATENT DOCUMENTS

| DE | 2229446 | | 2/1972 |
| GB | 1 108 841 A | | 5/1983 |
| JP | 61-268613 | | 11/1986 |
| JP | 63-54318 | | 3/1988 |
| JP | 10-017448 | | 1/1998 |
| JP | 20000063290 | | 2/2000 |
| JP | 2001 114659 A2 | | 4/2001 |
| WO | WO 93/19152 | * | 9/1993 |
| WO | WO 94/02022 | * | 2/1994 |
| WO | WO 98/43594 | | 10/1998 |
| WO | WO 99/18140 | | 4/1999 |
| WO | WO 99/42079 | | 8/1999 |
| WO | WO 99/62472 | | 12/1999 |
| WO | WO 00/00165 | | 1/2000 |
| WO | WO 00/33792 | | 6/2000 |
| WO | WO 00/65911 | | 11/2000 |

OTHER PUBLICATIONS

Kirk–Othrom Encyclopedia of Chemical Technology 4$^{th}$ vol. 6 pp 892–944 Colorants for Foods Drugs Cosmetics & Medical Devices, (1993).*

(Continued)

Primary Examiner—Frederick F. Krass
(74) Attorney, Agent, or Firm—Betty J. Zea

(57) ABSTRACT

The present invention relates to compositions comprising: (a) from about 15% to about 70% by weight of the composition of a denture adhesive component; (b) a safe and effective amount of a colorant selected from the group consisting of xanthene dyes, fluorescein dyes, free acids and salts thereof, and mixtures thereof; and (c) a safe and effective amount of a non-aqueous denture adhesive carrier. The present invention further relates to a method of reducing, inhibiting and/or preventing, calculus, tartar, plaque, stain, and/or microbes in the oral cavity, by applying the above denture adhesive composition to the oral cavity of a denture wearer in need thereof. The present invention further relates to a method of providing improved antimicrobial effects in the oral cavity by applying the above denture adhesive composition to the oral cavity of a denture wearer in need thereof.

24 Claims, No Drawings

U.S. PATENT DOCUMENTS

| | | |
|---|---|---|
| 5,055,046 A | 10/1991 | Chaudhuri et al. |
| 5,064,658 A | 11/1991 | Cherukuri et al. |
| 5,087,460 A | 2/1992 | Cherukuri et al. |
| 5,093,387 A * | 3/1992 | Schobel et al. ............. 523/120 |
| 5,096,699 A | 3/1992 | Gaffar et al. |
| 5,110,607 A | 5/1992 | Yang |
| 5,114,718 A | 5/1992 | Damani |
| 5,166,233 A | 11/1992 | Kuroya et al. |
| 5,185,386 A | 2/1993 | Cohen et al. |
| 5,192,362 A | 3/1993 | Harvey et al. |
| 5,208,009 A | 5/1993 | Gaffar et al. |
| 5,266,335 A | 11/1993 | Cherukuri et al. |
| 5,304,616 A | 4/1994 | Rajaiah et al. |
| 5,310,563 A | 5/1994 | Curtis et al. |
| 5,326,685 A | 7/1994 | Gaglio et al. |
| 5,334,375 A | 8/1994 | Nabi et al. |
| 5,340,314 A | 8/1994 | Tarvis |
| 5,368,844 A | 11/1994 | Gaffar et al. |
| 5,424,058 A | 6/1995 | Rajaiah et al. |
| 5,496,541 A | 3/1996 | Cutler |
| 5,498,429 A | 3/1996 | Orlandi et al. |
| 5,543,443 A | 8/1996 | Rajaiah et al. |
| 5,560,379 A | 10/1996 | Pieczenik |
| 5,569,477 A | 10/1996 | Nesbitt |
| 5,578,336 A | 11/1996 | Monte |
| 5,626,896 A | 5/1997 | Moore et al. |
| 5,639,445 A | 6/1997 | Curtis et al. |
| 5,658,586 A | 8/1997 | Rajaiah et al. |
| 5,713,738 A | 2/1998 | Yarborough |
| 5,750,591 A * | 5/1998 | Clarke et al. ............... 523/120 |
| 5,753,723 A * | 5/1998 | Chang et al. ............... 523/120 |
| 5,763,554 A * | 6/1998 | Prosise et al. ............. 523/120 |
| 5,866,179 A | 2/1999 | Testa |
| 5,872,160 A | 2/1999 | Rajaiah et al. |
| 5,872,161 A * | 2/1999 | Liang et al. ............... 523/120 |
| 5,877,233 A * | 3/1999 | Liang et al. ............... 523/120 |
| 5,880,172 A * | 3/1999 | Rajaiah et al. ............. 523/120 |
| 5,891,453 A | 4/1999 | Sagel et al. |
| 5,900,230 A | 5/1999 | Cutler |
| 6,046,291 A | 4/2000 | Zhang et al. |
| 6,069,188 A * | 5/2000 | Rajaiah et al. ............. 523/120 |
| 6,083,421 A | 7/2000 | Huang et al. |
| 6,117,416 A | 9/2000 | Prosise et al. |
| 6,124,374 A * | 9/2000 | Kolias et al. ............... 523/120 |
| 6,174,514 B1 | 1/2001 | Cherukuri et al. |
| 6,315,987 B1 | 11/2001 | Plochocka |
| 6,355,706 B1 * | 3/2002 | Rajaiah et al. ............. 523/120 |
| 6,475,497 B1 * | 11/2002 | Rajaiah et al. ............. 523/120 |
| 6,475,498 B1 * | 11/2002 | Rajaiah et al. ............. 523/120 |

OTHER PUBLICATIONS

U.S. Registered Trademark 1554178 CAS Registry Number Providine Numerical Identification of Chemical Substances ACS American Chemical Society Aug. 29, 1989.*

U.S. Abandoned Trademark Appn. 73713 167 Registry Number American Chemical Society—Abandoned Aug. 8, 1989.*

Shannon Bell USPTO Trademark Law Librarian to Shep Rose Results of Sercia for "CAS Registry Number" and "Registry Number" Eric Shively (ACS) To Shep Rose G USPTO.Gov, Feb. 24, 2003.*

L.A. Ray, Antimicrobial Activity of Phloxine B Against Listeria Monocytogenes, *Escherichia coli* and *Saccharomyces cerevisiae*; ASM 100th General Meeting, Los Angeles, CA.

Y. Yoke Marchang, Photodecomposition of Naturally Occurring Biocides, 1987 American Chemical Society, 1987, pp. 168–175, Light—Activated Pesticides.

Kukident Label.

M. Wilson, et al; Prevention of Bacterial Adhesion to Denture Acrylic, 1989, Journal of Dentistry—17; No 4, pp. 166–170.

* cited by examiner

COMPOSITIONS AND METHODS TO INHIBIT TARTAR AND MICROBES USING DENTURE ADHESIVE COMPOSITIONS WITH COLORANTS

This application is a continuation-in-part of U.S. Ser. No. 09/716,766, filed Nov. 20, 2000, now U.S. Pat. No. 6,475,497, which claims the benefit of U.S. Provisional Application No. 60/169,703, filed Dec. 8, 1999; and is a continuation-in-part of U.S. Ser. No. 09/716,820, filed Nov. 20, 2000, now U.S. Pat. No. 6,475,498, which claims the benefit of U.S. Provisional Application No. 60/169,558 filed Dec. 8, 1999; and is a continuation-in-part of U.S. Ser. No. 09/716,810, filed Nov. 20, 2000, now U.S. Pat. No. 6,677,391, which claims the benefit of 60/169,702 filed Dec. 8, 1999.

BACKGROUND OF THE INVENTION

Ordinary removable dentures, dental plates and the like, comprise teeth mounted in a suitable plate or base. Denture stabilizers are used to fill the interstices between the dentures and the gums or tissues. Prior to placement of the denture in the oral cavity, a denture stabilizer is applied to the denture-plate surface, which, for a perfect fit, should uniformly contact the gums and mucous tissues. The denture stabilizer is formulated not only for its adherent properties, but also to provide a cushion or gasket between the denture and the gums or tissues, thereby positioning the denture securely in the oral cavity.

Considerable effort has been made over the years to develop improved denture adhesive compositions. Both synthetic and natural polymers and gums have been used alone, in combination, and in combination with various other adhesives and other materials in an attempt to improve hold and reduce oozing of the adhesive from under the dental plate, and to reduce messiness and difficulty of removing the residual adhesive from the mouth and dentures. For example, alkyl vinyl ether-maleic copolymers and salts thereof are known for providing adequate hold in denture adhesive compositions. Such disclosures include: U.S. Pat. No. 3,003,988, Germann et al., issued Oct. 10, 1961; U.S. Pat. No. 4,980,391, Kumar et al., issued Dec. 25, 1990; U.S. Pat. No. 5,073,604, Holeva et al., issued Dec. 17, 1991; U.S. Pat. No. 5,525,652, Clarke, issued Jun. 11, 1996; U.S. Pat. No. 5,340,918, Kittrell et al., issued Aug. 23, 1994; U.S. Pat. No. 5,830,933, Synodis et al., issued Nov. 3, 1998, all of which are herein incorporated by reference.

In addition to adhesion, it is desirable to deliver anticalculus, antiplaque, antitartar, or antimicrobial benefits via the use of a denture adhesive composition especially for those denture wearers who still have some natural teeth remaining. Tartar is a deposit, which forms on the surfaces of teeth. Mature calculus consists of an inorganic portion which is largely calcium phosphate arranged in a hydroxyapatite crystal lattice structure similar to bone, enamel and dentine. An organic portion is also present and consists of desquamated epithelial cells, leukocytes, salivary sediment, food debris, and microorganisms.

It is generally known that certain polysaccharides applied via an aqueous carrier may prevent specific types of bacteria from adhering to denture acrylic. Wilson et al., Prevention of bacterial adhesion to denture acrylic, *J. Dent* 1989; Vol. 17; p. 166–70 and U.S. Pat. No. 5,192,362, Harvey et al., issued Mar. 9, 1993. However, only aqueous compositions of polysaccharides were tested and applied to acrylic strips. In addition, the '362 patent is not concerned with anhydrous compositions or the securing of dentures. The dentures are coated from an aqueous suspension. In addition U.S. Pat. No. 4,315,779, issued Feb. 16, 1982, Heyd et al., teaches a non-adhesive denture composition for improving the fit and adaptation of dentures to the oral cavity comprising cellulose polymer or alginate, a demulcent selected from glycerine, sorbitol, and propylene glycol, and 50% to 95% by weight water. This reference also teaches that these compositions prevent the build-up of undesirable deposits such as plaque and have antibacterial and/or mycostatic effects.

Despite the above-noted technologies, a need still exists for denture stabilizing compositions providing not only improved hold but also anticalculus, antiplaque, antitartar, antistain and antimicrobial benefits to the denture wearer. The present invention relates to compositions and methods of reducing, inhibiting, preventing, calculus, tartar, plaque, stain and/or microbes, in the oral cavity of a denture wearer in need thereof, by applying to the oral cavity, an effective amount of non-aqueous denture adhesive composition comprising an effective amount of a colorant, a denture adhesive component, and a non-aqueous denture adhesive carrier. These compositions provide the above benefits, while providing superior denture hold, holding dentures in place for a prolonged period of time.

SUMMARY OF THE INVENTION

The present invention relates to compositions comprising:
(a) from about 15% to about 70% by weight of the composition of a denture adhesive component;
(b) from 0.006% to about 10% by weight of the composition of a colorant selected from the group consisting of xanthene dyes, fluorescein dyes, free acids and salts thereof, and mixtures thereof; and
(c) a safe and effective amount of a non-aqueous denture adhesive carrier.

The present invention further relates to compositions comprising:
(a) from about 15% to about 70% by weight of the composition of a denture adhesive component;
(b) from about 0.0001% to about 10% by weight of the composition of a colorant selected from the group consisting of CAS Numbers 518-47-8; 6417-85-2; 2321-07-5; 596-03-2; 17372-87-1; 548-26-5; 1326-05-2; 15086-94-9; 6441-77-6; 18472-87-2; 15876-58-1; 33239-19-9; 38577-97-8; 16423-68-0; 632-68-8; 632-69-90; 24545-86-6; 3520-42-1; 81-88-930; 6252-76-2; 5873-16-5; 12220-28-9; 66225-66-9; 989-38-8; 12224-98-5; 81-88-9; 509-34-2; 1326-03-0; 2390-63-8; 81-37-8; 6539-22-4 lakes thereof, and mixtures thereof; and
(c) a safe and effective amount of a non-aqueous denture adhesive carrier.

The present invention further relates to a method of reducing, inhibiting and/or preventing, calculus, tartar, plaque, stain, and/or microbes in the oral cavity, by applying the above denture adhesive compositions to the oral cavity of a denture wearer in need thereof. The present invention further relates to a method of providing improved antimicrobial effects in the oral cavity by applying the above denture adhesive compositions to the oral cavity of a denture wearer in need thereof.

DETAILED DESCRIPTION OF THE INVENTION

A detailed description of essential and optional components of the present invention is given below.

Definitions

The term "safe and effective adhesive amounts" as used herein means an amount sufficient to provide adherence to the oral cavity and/or provide adherence of a dental prosthesis to the oral cavity, without toxicity to the user or damage to oral tissue.

Also, "safe and effective amount", as used herein, is meant an amount of an agent high enough to significantly (positively) modify the condition to be treated, but low enough to avoid serious side effects (at a reasonable benefit/risk ratio), within the scope of sound medical/dental judgment. The safe and effective amount of an agent may vary with the particular condition being treated, the age and physical condition of the patient being treated, the severity of the condition, the duration of treatment, the nature of concurrent therapy, the specific form of the source employed, and the particular vehicle from which the agent is applied.

The term "AVE/MA" as used herein refers to alkyl vinyl ether-maleic acid or anhydride copolymer. The term "AVE/MA/IB" refers to terpolymers with alkyl vinyl ether, maleic acid or anhydride, and isobutylene. The term "mixed polymer salts" or "mixed salts", as used herein, refers to salts of AVE/MA and/or salts of AVE/MA/IB where at least 2 different cations are mixed on the same polymer with each other or with other salts.

The term "free acid" or "FA" component, as used herein, refers either to the unreacted carboxyl groups (—COOH) of AVE/MA copolymer and/or AVE/MA/IB plus any other monovalent cations of carboxyl groups (e.g., COONa) of the polymer. Monovalent cations include Group IA cations, such as sodium, potassium, hydrogen, etc. Preferably, the term "free acid" refers to the unreacted carboxyl groups (—COOH) of AVE/MA and/or AVE/MA/IB plus sodium and potassium cations. More preferably, the term "free acid" refers only to the unreacted carboxyl groups (—COOH) of the AVE/MA and/or AVE/MA/IB.

The percentages used herein to describe the cationic salt function of the alkyl vinyl ether-maleic acid or anhydride copolymers are defined as the stoichiometric percent of the total initial carboxyl groups reacted on the polymer.

All other percentages used herein are by weight of the composition unless otherwise indicated.

Denture Adhesive Component

The present invention comprises a safe and effective adhesive amount of a denture adhesive component, generally at a level of from about 10% to about 90%, in another embodiment from about 15% to about 70%, in another embodiment from about 20% to about 50%, and in another embodiment from about 25% to about 45%, by weight of the composition. In one embodiment the compositions of the present invention comprise at least 20 percent by weight, and in another embodiment at least 30 percent by weight of the composition, of a denture adhesive component.

"Denture adhesive components" can be any bioadhesive materials and include natural gums, synthetic polymeric gums, AVE/MA, salts of AVE/MA, AVE/MA/IB, salts of AVE/MA/IB, synthetic polymers, mucoadhesive polymers, water-soluble hydrophilic colloids or polymers having the property of swelling upon exposure to moisture to form a mucilaginous mass, hydrophilic polymers, saccharide derivatives, cellulose derivatives, any adhesive material employed in denture stabilizing compositions, and mixtures thereof. Examples of such materials include karaya gum, guar gum, gelatin, algin, sodium alginate, tragacanth, chitosan, polyethylene glycol, polyethylene oxide, acrylamide polymers, polyacrylic acid, homopolymer of acrylic acid cross linked with an allyl ether of pentaerythritol or an allyl ether of sucrose, polyvinyl alcohol, polyamines, polyquarternary compounds, ethylene oxide polymers, polyvinylpyrrolidone, cationic polyacrylamide polymers, AVE/MA, AVE/MA/IB, mixed salts of AVE/MA, mixed salts of AVE/MA/IB, and mixtures thereof.

In one embodiment the adhesives are AVE/MA, salts of AVE/MA, salts of AVE/MA/IB, mixed salts of AVE/MA, mixed salts of AVE/MA/IB, cellulose derivatives (such as methylcellulose, carboxymethylcellulose, hydroxyethylcellulose, hydroxypropylcellulose, hydroxypropylmethylcellulose, and mixtures thereof), polyethylene glycol, polyethylene oxide, karaya gum, sodium alginate, chitosan, polyvinyl alcohol, and mixtures thereof. In yet another embodiment, the adhesive component is AVE/MA, salts of AVE/MA, mixed salts of AVE/MA, cellulose derivatives and mixtures thereof.

Alkyl Vinyl Ether-Maleic Copolymer

In one embodiment of the invention the denture adhesive component is AVE/MA or salts of AVE/MA. The alkyl vinyl ether-maleic acid co-polymer comprises, or consists essentially of, the repeated structural unit:

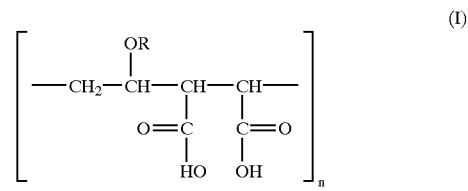

(I)

wherein R represents an alkyl radical, preferably a $C_1$ to $C_5$ alkyl radical, n is an integer greater than one representing the number of repeated occurrences of the structural unit in a molecule of the polymer.

In one embodiment, the adhesive component is AVE/MA and salts thereof, preferably mixed salts of AVE/MA, wherein the copolymer contains a cationic salt function comprising a cation selected from the group consisting of Group IA and Group 2A cations of the periodic table, yttrium, titanium, zirconium, vanadium, chromium, manganese, iron, nickel, copper, zinc, boron, aluminum, cations and mixtures thereof. In another embodiment, the adhesive component is a mixed salt of AVE/MA containing a cationic salt function comprising a cation selected from the group consisting of strontium, zinc, iron, boron, aluminum, vanadium, chromium, manganese, nickel, copper, yttrium, titanium, magnesium, calcium, sodium, cations and mixtures thereof, and in yet another embodiment the cation is selected from the group consisting of strontium, zinc, iron, magnesium, calcium, sodium, cations, and mixtures thereof.

AVE/MA contains, in one embodiment, a cationic salt function comprising from about 5% to about 50%, in another embodiment, from about 10% to about 40%, in yet another embodiment, from about 10% to about 35% (of the total initial carboxyl groups reacted) zinc cations. These zinc cations can be mixed with other cations selected from the group consisting of strontium, calcium, magnesium and mixtures thereof at a level of from about 5% to about 65%, preferably from about 10% to about 50%. These salts optionally can further comprise from about 0.001% to about 2.5%, preferably from about 0.01% to about 2% of iron, boron, aluminum, vanadium, chromium, manganese, nickel, copper, yttrium, and/or titanium cations.

AVE/MA and salts thereof and AVE/MA/IB and salts thereof, are also described in U.S. Pat. No. 5,073,604 to Holeva et al., issued Dec. 17, 1991; U.S. Pat. No. 5,525,652, issued Jun. 11, 1996, Clarke et al.; U.S. Pat. No. 4,758,630, issued Jul. 19, 1988, Shah et al.; 5,304,616, issued Apr. 19, 1994, Rajaiah et al.; U.S. Pat. No. 5,424,058, issued Jun. 13, 1995, Rajaiah; U.S. Pat. No. 5,424,058, issued Jun. 13, 1995, Rajaiah et al.; U.S. Pat. No. 4,758,630, issued Jul. 19, 1988, Shah et al.; U.S. Pat. No. 5,830,933, issued Nov. 3, 1998, Synodis et al.; U.S. Pat. No. 2,047,398, issued Jul. 14, 1936, Voss et al.; U.S. Pat. No. 3,003,988, issued Oct. 10, 1961, Germann et al.; U.S. Pat. No. 5,880,172, Rajaiah et al., issued Mar. 9, 1999; U.S. Pat. No. 5,900,470, Prosise et al., issued May 4, 1999; U.S. Pat. No. 5,037,924, Tazi et al., issued Aug. 6, 1991; U.S. Pat. No. 5,082,913, Tazi et al., issued Jan. 21, 1992; U.S. Pat. No. 6,239,191, Wong et al., issued May 29, 2001; U.S. Pat. No. 6,276,937, Gasman et al., issued Aug. 21, 2001; U.S. Pat. No. 6,025,411, Wong et al., issued Feb. 15, 2002; all of which are incorporated herein by reference in their entirety. Salts of AVE/MA are also described in P&G patents and copending applications Ser. Nos.: 60/152,158, filed Sep. 2, 1999, Rajaiah et al.; U.S. Pat. No. 6,355,706, 1999, Rajaiah et al.; 60/129,162, filed Apr. 14, 1999, Rajaiah et al.; 60/152,122, filed Sep. 2, 1999, Rajaiah et al.; 09/291,554, filed Apr. 14, 1999, Rajaiah et al.; now abandoned 09/389,209, filed Sept. 2, 1999, Rajaiah et al.; now U.S. Pat. No. 6,617,374; all of which are incorporated herein by reference in their entirety.

In one embodiment the free acid level of the salts of the AVE/MA or AVE/MA/IB is at least about 36%, in another embodiment is from about 36% to about 60%, and even in another embodiment is from about 40% to about 55%, of the total initial carboxyl groups of the copolymer or terpolymer.

The specific viscosity of the starting copolymer acid or copolymer anhydride is from about 1.2 to about 14, when preferably measured in a 1% weight/volume solution in MEK (methyl ethyl ketone) at 25° C. Other methods and solvents can be used to measure the specific viscosity such as a 1% weight/volume solution in DMF (dimethyl formamide) at 25° C. and a 1% weight/volume solution in 2-butanone at 25° C.

Suitable AVE/MA copolymers may be prepared by well-known methods of the prior art; see, for example, U.S. Pat. Nos. 2,782,182, and 2,047,398, both of which are incorporated by reference herein in their entirety.

The salt form of the subject polymers may be prepared by the interaction of the acid or anhydride polymer with at least one cationic salt function as described above, having a functional group typical of reactants of a carboxylic acid, such as, for example, the hydroxide, oxide, acetate, halide, lactate, etc. in an aqueous medium. In one embodiment, the zinc oxide, strontium carbonate, iron sulfate n-hydrate, etc. are utilized.

Ions that form toxic, irritating or contaminating by-products should be avoided, or special precautions and treatment provided to assure the removal and absence of such by-products from the polymeric salt end product. The particular compound used should be substantially pure to assure obtaining a substantially pure, polymeric salt end product.

The salt form of the polymer can be made by mixing the salts (sodium hydroxide, zinc oxide, strontium carbonate, ferric sulfate n-hydrate, calcium hydroxide and/or magnesium oxide, etc.) in an aqueous dispersion. This is combined with the powder alkyl vinyl ether-maleic acid or anhydride copolymer, in the form of a slurry, in an amount sufficient to provide the desired cationic content desired in the end product. This is done at ambient temperature and then slowly heated to 70°–95° C. with continuous vigorous mixing so as to prevent localized precipitation of the cationic polymeric salt; mixing is continued to ensure that all the salt forming compound is reacted with the copolymer.

Alternatively, the AVE/MA copolymer is hydrolyzed and neutralized in an aqueous mixture or slurry of one or more divalent and/or monovalent metal bases by heating the copolymer/base mixture to a temperature ranging from about 45° C. to about 100° C.

In either of the above processes, the resulting slurry or solution is transferred to shallow stainless steel drying trays and placed in a forced air mechanical convection oven at 60°–70° C. for a time sufficient to evaporate the reaction medium (water) and remove water from the copolymer (about 18–24 hours). Alternatively, the resulting slurry or solution can be drum-dried at 100° to 200° C. with hot steam to evaporate the water content and recover the copolymer in the flake form. After drying, the polymer forms brittle flakes, which can easily be peeled off from the trays or drum surface and ground to a fine powder as desired to provide satisfactory denture stabilizing properties. Methods of making these mixed salts of AVE/MA polymers are further disclosed in U.S. Pat. No. 5,073,604, Holeva et al., issued Dec. 17, 1991 and U.S. at. No. 5,872,161, Liang et al., issued Feb. 16, 1999, both of which are herein incorporated by reference in their entirety.

Antimicrobial Colorants/Dyes

The present invention also comprises a safe and effective amount of an antimicrobial colorant or dye selected from the group consisting of xanthene dyes, fluorescein dyes, free acid and salts thereof, and mixtures thereof. The colorant is generally used at a level of from about 0.00001% to about 10%, in another embodiment from about 0.0001% to about 5%, in another embodiment from about 0.009% to about 2%, in another embodiment from about 0.01% to about 1%, in yet another embodiment from about 0.05% to about 1% and in another embodiment from about 0.1% to about 0.5%, by weight of the composition.

Xanthene dyes include the group of dyes whose molecular structure is related to that of xanthene. Xanthene is the central structure of the fluorescein, eosin, and rhodamine dyes. The aromatic ($C_6H_4$) groups of xanthene dyes constitute the chromophore. These xanthene dyes are closely related structurally to diaryl methane dyes.

In one embodiment the colorants are selected from the group consisting of (including salts, sodium salts, potassium salts, free acids, free bases, and mixtures thereof)[1]:

TABLE 1

| Color Index Name | CAS Number and CI Number | Other Names | Description/ Chemical Name |
| --- | --- | --- | --- |
| Acid Yellow 73 | 518-47-8 CI No. 45350 | Yellow No. 11 (EC-former) Yellow No. 202(1) (Japan) | Fluorescein sodium salt Hydroxy-Phthaleins |

TABLE 1-continued

| Color Index Name | CAS Number and CI Number | Other Names | Description/ Chemical Name |
|---|---|---|---|
| | | D&C Yellow No. 8 (US) Uranine Na Salt (Other) | |
| Acid Yellow 73 | 6417-85-2 CI 45350 | Yellow No. 202(2) (Japan) Uranine K Salt (Other) | Hydroxy-Phthaleins Fluorescein potassium salt |
| Acid Yellow 73 | 2321-07-5 CI 45350:1 | Yellow No. 201 (Japan) D&C Yellow No. 7 (US) Fluorescein Free Acid (Other) | Hydroxy-Phthaleins Fluorescein free acid |
| Solvent Red 72 | 596-03-2 CI 45370:1 | Red No. 17 (EC-former) Orange No. 201 (Japan) D&C Orange No. 5 (US) Dibromo Fluorescein Free Acid (Other) | Hydroxy-Phthaleins 4,5-Dibrom-fluorescin, free acid 4,5-Dibrom-fluorescin, sodium salt (CI 45370) |
| Acid Red 87 | 17372-87-1 CI 45380 | Red No. 18 (EC-former) Red No. 230(1) (Japan) D&C Red No. 22 (US) Eosine Na Salt (Other) | Hydroxy-Phthaleins (sodium salt) |
| Acid Red 87 | 548-26-5 CI 45380 | Red No. 230(2) (Japan) Eosine K Salt (Other) | Hydroxy-Phthaleins (potassium salt) |
| Pigment Red 90 | 1326-05-2 CI 45380:1 | | |
| Solvent Red 43 | 15086-94-9 CI 45380:2 or :1 | Red No. 18 (EC-former) Red No. 223 (Japan) D&C Red No. 21 (US) Tetrabromo Fluorescein Free Acid | Hydroxy-Phthaleins (free acid) |
| Acid Red 98 | 6441-77-6 CI 45405 | Phloxine Na Salt (Other) | 2,4,5,7-Tetrabrom-3"6"-dicloro-fluorescin, potassium salt |
| Acid Red 92 | 18472-87-2 CI 45410 | Red No. 20 (EC-former) Red No. 104(1) (Japan) D&C Red No. 28 (US) Phloxine B Na Salt (Other) | Hydroxy-Phthaleins 2,4,5,6-tetrabromo-3',4',5',6'-tetrachloro-fluorescein, sodium salt |
| Acid Red 92 | 13473-26-2 CI 45410 | Red No. 231 (Japan) Phloxine B K Salt (Other) | Hydroxy-Phthaleins Potassium salt |
| Solvent Red 48 | 13473-26-2 CI 45410:1 | Red No. 218 (Japan) D&C Red No. 27 (US) Phloxine B Free Acid (Other) | Hydroxy-Phthaleins 2,4,5,6-tetrabromo-3',4',5',6'-tetrachloro-fluorescein free acid |
| Acid Red 92/Pigment Red 174 | 15876-58-1 CI 45410:2 | | |
| Acid Red 95 | 33239-19-9 CI 45425 | Red No. 21 (EC-former) Orange No. 207 (Japan) | 2,4-Diiodide-fluorescin, sodium salt |

TABLE 1-continued

| Color Index Name | CAS Number and CI Number | Other Names | Description/ Chemical Name |
|---|---|---|---|
| | | D&C Orange No. 11 (US) Diiodo Fluorescein Na Salt (Other) | Hydroxy- Phthaleins |
| Solvent Red 73 | 38577-97-8 CI 45425:1 | Orange No. 206 (Japan) D&C Orange No. 10 (US) Diiodo Fluorescein Free Acid (Other) | 2,4- Diiodide- fluorescin, free acid Hydroxy- Phthaleins 2,4- Diiodide- fluorescin, aluminum lake (CI 45425:2) |
| Acid Red 51/Food Red 14 | 16423-68-0 CI 45430 | Red No. 22 (EC-former) Red No. 3 (Japan) FD&C Red No. 3 (US) Erythrosine Na Salt (Other) | 2,4,5,7- Tetraiodide- fluorescin, sodium salt Hydroxy- Phthaleins |
| Pigment Red 172 | 12227-78-0 CI 45430:1 | | 2,4,5,7- Tetraiodide- fluorescin, aluminum lake 2,4,5,7- Tetraiodide- fluorescin, free acid (CI 45430:2 - Solvent Red 140) |
| Acid Red 94 | 632-68-8 CI 45440 | Red No. 232 (Japan) Rose Bengal K Salt (Other) | Hydroxy- Phthaleins |
| Acid Red 94 | 632-69-90 CI 45440 | Red No. 105(1) (Japan) Rose Bengal Na Salt (Other) | 2,4,5,7- tetraiodide- 3',4',5',6'- tetrochloro fluorescein sodium salt or potassium salt |
| Solvent Orange 16 | 24545-86-6[2] CI 45396 | | Xanthene dye 4,5-Dinitro- fluorescin, free acid Hydroxy- Phthaleins |
| C.I.Acid Red 52 | 3520-42-1 CI 45100 | Red No. 102 (Japan) Sulforhodamin B | Xanthene dye 3,6- Bis(diethyl- amino)-9- (2,4- disulfo- phenyl)-xanthyl- immonium, sodium salt |
| C.I. Basic Violet | 81-88-930 CI 45170 | Rhodamin B | Xanthene dye 3,6- Bis(diethyl- amino)-9- (2'benzoic acid)- xanthyl- immonium, chloride (X) CI 45170:1 (free base) |

TABLE 1-continued

| Color Index Name | CAS Number and CI Number | Other Names | Description/ Chemical Name |
|---|---|---|---|
| C.I. Acid Violet 9 | 6252-76-2 CI 45190 | Red No. 401 (Japan) | Xanthene 3-m-Toluidine-6-m-toluidine-p-sulfo acid-9(2-benzoic acid)-xanthyl-immonium, Sodium salt |
| C.I. Acid Red 50 | 5873-16-5 CI 45220 | Sulforhodamin G | Xanthene 3,6-Bis(diethyl-amino)-2,7-dimethyl-9-(2,4-disulfo-phenyl)-)-xanthyl-immonium, sodium salt |
| Acid Red 289 | 12220-28-9 | | |
| Solvent Violet 10 | 66225-66-9 | | |
| Basic Red 1 | 989-38-8 CI 45160 | Rhodamine 6G | |
| Pigment Red 81 | 12224-98-5 CI 45160:1 | | |
| Basic Violet 10 | 81-88-9 CI 45170 | Rhodamine | |
| Solvent Red 49 | 509-34-2 CI 45170:1 | Rhodamine B Base | |
| Pigment Violet 1 | 1326-03-0 CI 45170:2 | | |
| Basic Violet 11 | 2390-63-8 CI 45175 | Fanal Red 6BM (IG) | |
| Solvent Green 4 | 81-37-8 CI 45550 | Fluorescent Brightener 74 | |
| Mordant Red 27 | 6539-22-4 CI 45180 | Chromoxane Brilliant Red | |

[1]See the CTFA International Color Handbook, 2$^{nd}$ Ed., The Cosmetic, Toiletry, and Fragrance Association, Inc., 1985, 1992, Including pp. 185–201. Also see, Coloring of Food, Drugs, and Cosmetics, G. Otterstatter, Marcel Dekker, Inc. 1999, including Chapter 9 pp. 222–236.
[2]Sigma Aldrick Product No. 35,882-7: C2OH10N2O9.

In another embodiment the colorant is selected from the group consisting of CAS Numbers 518-47-8; 64.17-85-2; 2321-07-5; 596-03-2; 17372-87-1; 548-26-5; 1326-05-2; 15086-94-9; 6441-77-6; 18472-87-2; 13473-26-2, 15876-58-1; 33239-19-9; 38577-97-8; 16423-68-0; 12227-78-0, 632-68-8; 632-69-90; 24545-86-6; 3520-42-1; 81-88-930; 6252-76-2; 5873-16-5; 12220-28-9; 66225-66-9; 989-38-8; 12224-98-5; 81-88-9; 509-34-2; 1326-03-0; 2390-63-8; 81-37-8; 6539-22-4, salts and free acids thereof, lakes thereof, and mixtures thereof.

In another embodiment the colorant is selected from the group consisting of CAS Numbers 518-47-8; 6417-85-2; 2321-07-5; 596-03-2; 17372-87-1; 548-26-5; 1326-05-2; 15086-94-9; 6441-77-6; 18472-87-2; 15876-58-1; 33239-19-9; 38577-97-8; 16423-68-0; 632-68-8; 632-69-90; 24545-86-6; 3520-42-1; 81-88-930; 6252-76-2; 5873-16-5; 12220-28-9; 66225-66-9; 989-38-8; 12224-98-5; 81-88-9; 509-34-2; 1326-03-0; 2390-63-8; 81-37-8; 6539-22-4, lakes thereof, and mixtures thereof.

In another embodiment the colorant is selected from the group consisting of CAS Numbers 518-47-8; 6417-85-2; 2321-07-5; 596-03-2; 17372-87-1; 548-26-5; 1326-05-2; 15086-94-9; 6441-77-6; 33239-19-9; 38577-97-8; 632-68-8; 632-69-90; 24545-86-6; 3520-42-1; 81-88-930; 6252-76-2; 5873-16-5; 12220-28-9; 66225-66-9; 989-38-8; 12224-98-5; 81-88-9; 509-34-2; 1326-03-0; 2390-63-8; 81-37-8; 6539-22-4, lakes thereof, and mixtures thereof In another embodiment the colorant is selected from the group consisting of CAS numbers 596-03-2; 17372-87-1; 548-26-5; 1326-05-2, 15086-94-9; 6441-77-6; 18472-87-2; 13473-26-2; 13473-26-3; 33239-19-9; 38577-97-8; 16423-68-0; 12227-78-0; 632-68-8; 632-69-90; 24545-86-6; 3520-42-1; 3520-42-1; 5873-16-5, lakes thereof, sodium or potassium salts thereof, free acids or bases thereof, and mixtures thereof. In even another embodiment the colorant is selected from the group consisting of CAS Numbers 596-03-2; 17372-87-1; 548-26-5; 1326-05-2, 15086-94-9; 6441-77-6; 18472-87-2; 13473-26-2; 13473-26-3; 15876-58-1, 33239-19-9; 38577-97-8; 12227-78-0; 16423-68-0, 632-68-8; 632-69-90; 24545-86-6; 3520-42-1; 3520-42-1; 5873-16-5, lakes thereof, and mixtures thereof. In another embodiment the colorant is selected from the group consisting of CAS Numbers 596-03-2; 17372-87-1; 548-26-5; 1326-05-2, 15086-94-9; 6441-77-6; 18472-87-2; 13473-26-2; 15876-58-1, 13473-26-3; 33239-19-9; 38577-97-8; 632-68-8; 632-69-90; 24545-86-6; 3520-42-1; 3520-42-1; 5873-16-5, lakes thereof, and mixtures thereof; and in another embodiment is selected from the group consisting of CAS numbers 16423-68-0, 12227-78-0, 16423-68-0; 17372-87-1; 548-26-5, 1326-05-2, 18472-87-2; 13473-26-3; 13473-26-2, 15086-

94-9 and mixtures thereof; in another embodiment is selected from the group consisting of CAS numbers 12227-78-0, 17372-87-1; 548-26-5, 1326-05-2, 18472-87-2; 13473-26-3; 13473-26-2, 15086-94-9 and mixtures thereof; in another embodiment is selected from the group consisting of CAS numbers 17372-87-1; 548-26-5, 1326-05-2, 18472-87-2; 13473-26-3; 13473-26-2, 15086-94-9 and mixtures thereof; and in even another embodiment the colorant is selected from the group consisting of CAS no. 18472-87-2; CAS no. 13473-26-3, 13473-26-2, lakes thereof and mixtures thereof.

The term "colorant" as used herein includes any of the above dyes in the form of lakes (where the dye is bound with aluminum, aluminum oxide or aluminum hydrate) and lakes dispersed in liquids such as mineral oil and/or petrolatum, for example Opatint-OD 1646 wherein the colorant is a lake dispersed in liquid carrier like mineral oil or petrolatum.

In one embodiment the colorant is selected from the group consisting of paste-like Opatint® products from Colorcon (West Point, Pa.), Opatint-OD 1646, fluorescein dyes with chlorine and/or bromine, and mixtures thereof. In another embodiment the colorants are selected from the group consisting of paste-like Opatint® products from Colorcon (West Point, Pa.), Opatint-OD 1646, fluorescein dyes with chlorine and/or bromine, CAS no. 17372-87-1; CAS no. 18472-87-2; CAS no. 13473-26-2; and mixture thereof.

Fluorescein colorants can have chlorine and/or bromine and include tetrabromo-tetrachloro-fluorescein, and disodium salt of tetrabromo-tetrachloro-fluorescein. In another embodiment the dyes are selected from the group consisting of fluorescein dyes with chlorine and/or bromine, tetrabromo-tetrachloro-fluorescein, disodium salt of tetrabromo-tetrachloro-fluorescein, CAS no. 17372-87-1; CAS no. 18472-87-2; CAS no. 13473-26-2; lakes thereof and mixture thereof.

The above colorants are effective antimicrobial agents, against pathogens of the oral cavity, in non-aqueous denture adhesive compositions despite the higher amount of denture adhesive component present, the lack of water present in the compositions, and even at low levels of colorant. These colorants also provide improved antimicrobial efficacy against pathogens of the oral cavity, in non-aqueous denture adhesive compositions and provide improved calculus, tartar, plaque, or stain efficacy, in the oral cavity.

Non-Aqueous Denture Adhesive Carrier

The non-aqueous denture adhesive carrier is selected from the group consisting of a non-aqueous vehicle and a non-adhesive self-supporting layer. The level of non-aqueous vehicle is from 10% to about 90%, in another embodiment is from about 20% to about 80%, and in yet another embodiment is from about 20% to about 60%, by weight of the composition.

Non-aqueous Vehicles

The non-aqueous vehicle is generally any chemical in any physical form that does not contain water. The non-aqueous vehicle is selected from the group consisting of liquid petrolatum, petrolatum, mineral oil, glycerin, natural and synthetic oils, fats, silicone and silicone derivatives, polyvinyl acetate, natural and synthetic waxes such as animal waxes like beeswax, lanolin and shellac, hydrocarbons, hydrocarbon derivatives, vegetable oil waxes such as carnauba, candelilla and bayberry wax, vegetable oils such as caprylic/capric triglycerides, in another embodiment is selected from the group consisting of liquid petrolatum, petrolatum, mineral oil, vegetable oils such as corn, soy bean, cottonseed, castor, palm and coconut oils and animal oil such as fish oil and oleic acid, and mixtures thereof; and in yet another embodiment is mineral oil.

Vegetable oils comprised of saturated medium chain fatty acids such as caprylic acid, capric acid and mixtures thereof, may be used in the present invention. These vegetable oils and other non-aqueous vehicles for denture adhesive compositions are further described in U.S. Pat. No. 5,561,177, issued on Oct. 1, 1996, Khaledi et al., which is incorporated herein by reference in its entirety.

Non-Adhesive Self-Supporting Layer

The non-aqueous carrier can comprise at least one non-adhesive self-supporting layer. The non-adhesive self-supporting layer is characterized by its ability to maintain strength and provide integrity for the adhesive composition in the presence of water and/or saliva. The non-adhesive self-supporting layer may include materials such as polyester, polypropylene, nylon, rayon, cellulose acetate, non-adhesive cellulose derivatives, cloth, fibrous fleece, paper, plastic, leather, microcrystalline wax, synthetic fibers, natural fibers, and mixtures thereof. Preferred are non-adhesive cellulose derivatives, polyester, polypropylene, nylon, rayon, cloth, paper, microcrystalline wax, and mixtures thereof. More preferred are polyester, polypropylene, rayon, nylon, cloth and paper.

The non-adhesive self-supporting layer may be in any physical form suitable for providing strength and/or integrity to the present adhesive compositions. Such physical forms include non-woven, woven, continuous, chopped, foam, and combinations thereof. In addition, the non-adhesive self-supporting layer may be formed by any process commonly known in the art. Such processes include un-bonded, spray bonded, spun-bonded, needle-punched, carded, thermal bonded hydro entangled, melt blown, aperture print bonded, needled, wet-laid, dry-laid, and combinations thereof.

The present denture adhesive compositions, which comprise a non-adhesive self-supporting layer, may also comprise a coating, which is sticky to dry dentures, and, if present, will be placed on one side of the denture adhesive composition. Compositions suitable for use as this type of adhesive layer include silicones, rubbers, petrolatum, natural polymers, synthetic polymers, and mixtures thereof. The adhesive layer may be present at a level of from about 0% to about 70%, and in another embodiment from about 0.5% to about 20%, by weight of the composition.

Miscellaneous Carriers

Other suitable ingredients include miscellaneous colorants, preservatives (such as methyl and propyl parabens), thickeners such as silicon dioxide, and polyethylene glycol, which may be present at levels of from about 0% to about 20%, by weight of the composition.

Plasticizers

In addition one or more toxicologically acceptable plasticizers may also be included in the present compositions. The term "toxicologically-acceptable", as used herein, is used to describe materials that are suitable in their toxicity profile for administration to humans and/or lower animals. Plasticizers that may be used in the present compositions include dimethyl phthalate, diethyl phthalate, dioctyl phthalate, glycerin, diethylene glycol, triethylene glycol, Igepal®, Gafac®, sorbitol, tricresyl phosphate, dimethyl sebacate, ethyl glycolate, ethylphthalyl ethyl glycolate, o- and p-toluene ethyl sulfonamide, and mixtures thereof. Plasticizers may be present at a level of from about 0% to about 70%, in another embodiment from about 1% to about 30%, by weight of the compositions.

Flavors, Fragrance, Sensates

The compositions of the present invention may also include one or more components, which provide flavor, fragrance, and/or sensate benefit (warming or cooling agents). Suitable components include natural or artificial sweetening agents, menthol, menthyl lactate, wintergreen oil, peppermint oil, spearmint oil, leaf alcohol, clove bud oil, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, thymol, linalool, cinnamaldehyde glycerol acetal known as CGA, and mixtures thereof, as well as coolants. The coolant can be any of a wide variety of materials. Included among such materials are carboxamides, menthol, ketals, diols, and mixtures thereof. Preferred coolants in the present compositions are the paramenthan carboxyamide agents such as N-ethyl-p-menthan-3-carboxamide, known commercially as "WS-3", N,2,3-trimethyl-2-isopropylbutanamide, known as "WS-23," and mixtures thereof. Additional preferred coolants are selected from the group consisting of menthol, 3-1-menthoxypropane-1,2-diol known as TK-10 manufactured by Takasago, menthone glycerol acetal known as MGA manufactured by Haarmann and Reimer, and menthyl lactate known as Frescolat® manufactured by Haarmann and Reimer. The terms menthol and menthyl as used herein include dextro- and levorotatory isomers of these compounds and racemic mixtures thereof. TK-10 is described in U.S. Pat. No. 4,459,425, Amano et al., issued Jul. 10, 1984. WS-3 and other agents are described in U.S. Pat. No. 4,136,163, Watson, et al., issued Jan. 23, 1979; the disclosure of both are herein incorporated by reference in their entirety. These agents may be present at a level of from about 0% to about 50%, by weight of the composition.

Other Optional Ingredients

The denture adhesive compositions may also comprise one or more therapeutic actives suitable for topical administration. Therapeutic actives may be present at a level of from about 0% to about 70%, by weight of the composition, and in one embodiment from about 1% to about 20% by weight of the compostion. Therapeutic actives include antimicrobial agents such as iodine, tricolsan, peroxides, sulfonamides, bisbiguanides, or phenolics; antibiotics such as tetracycline, neomycin, kanamycin, metronidazole, or clindamycin; anti-inflammatory agents such as aspirin, acetaminophen, naproxen and its salts, ibuprofen, ketorolac, flurbiprofen, indomethacin, eugenol, or hydrocortisone; dentinal desensitizing agents such as potassium nitrate, strontium chloride or sodium fluoride; fluorides such as sodium fluoride, stannour fluoride, MFP; anesthetic agents such as lidocaine or benzocaine; anti-fungals such as those for the treatment of *candida albicans*; aromatics such as camphor, eucalyptus oil, and aldehyde derivatives such as benzaldehyde; insulin; steroids; herbal and other plant derived remedies; baking soda, and anti-neoplastics. It is recognized that in certain forms of therapy, combinations of these agents in the same delivery system may be useful in order to obtain an optimal effect. Thus, for example, an antimicrobial and an anti-inflammatory agent may be combined in a single delivery system to provide combined effectiveness.

Process for Preparation of the Composition

A process for preparing denture adhesive compositions of the present invention (creams, powders, wafers, non-aqueous liquids, aerosols, pastes) comprises conventional methods disclosed in the art. Conventional methods are taught in U.S. Pat. No. 5,525,652, issued Jun. 11, 1996, Clarke et al.; U.S. Pat. No. 3,003,988, issued Oct. 10, 1961, Germann et al.; U.S. Pat. No. 5,073,604, Holeva et al., issued Dec. 17, 1991; and U.S. Pat. No. 5,872,161, Liang et al., issued Feb. 16, 1999, all of which are herein incorporated by reference in their entirety.

A process for the preparation of the present denture adhesive compositions comprising a non-adhesive self-supporting layer, comprises coating a weighed amount of the adhesive components onto the non-adhesive self-supporting layer. This process is disclosed in U.S. Pat. No. 5,877,233, Liang et al, issued Mar. 2, 1999; U.S. Pat. No. 5,872,160, issued Feb. 16, 1999, Liang et al.; U.S. Pat. No. 5,880,172, Rajaiah et al., filed Oct. 25, 1996, all of which are incorporated herein by reference in their entirety.

Composition Use

The adhesive compositions may be in the form of a powder, cream, paste, non-aqueous liquid, aerosol, and/or wafer. Powder forms are sprinkled on a dental prosthesis, moistened and then inserted into the oral cavity. Wafer compositions (denture adhesive compositions with a self supporting layer) are thoroughly moistened and applied to denture prosthesis which are then inserted into the oral cavity. Cream, paste, aerosols, and non-aqueous liquid compositions are generally applied to the denture prosthesis and thereafter the denture is secured to the oral cavity.

EXAMPLES

The following examples further describe and demonstrate embodiments within the scope of the present invention. The examples are given solely for the purpose of illustration and are not to be construed as limitations of the present invention. Many variations of these are possible without departing from the spirit and scope of the invention.

Example I

A denture wearer places from 0.1 to 5 grams of any of the compositions described below on their denture. Then the subject inserts the denture into his/her mouth and presses it into place. After applying the composition, the composition prevents, reduces, inhibits, calculus, tartar, plaque, stain and/or microbes in the oral cavity.

|  | A Grams | B Grams | C Grams | D Grams | E Grams | F Grams | G Grams |
|---|---|---|---|---|---|---|---|
| White Mineral Oil | 23.95 | 23.95 | 23.95 | 23.95 | 23.95 | 23.95 | 23.95 |
| Petrolatum, White | 21.909 | 21.909 | 21.909 | 21.9 | 21.81 | 21.91 | 11.91 |
| Carboxymethylcellulose Sodium | 20.00 | 20.00 | 20.00 | 20.00 | 20.00 | 20.00 | 20.00 |
| Silicon Dioxide, Colloidal | 1.14 | 1.14 | 1.14 | 1.14 | 1.14 | 1.14 | 1.14 |
| D&C Red 27[3] (CAS 13473-26-2) | 0.00001 | 0.0001 | 0.001 | 0.01 | 0.1 | 1 | 10 |

-continued

|  | A Grams | B Grams | C Grams | D Grams | E Grams | F Grams | G Grams |
|---|---|---|---|---|---|---|---|
| Any salt, acid or anhydride of AVE/MA and/or AVE/MA/IB | 33.00 | 33.00 | 33.00 | 33.00 | 33.00 | 33.00 | 33.00 |

The colorant and non-aqueous carriers (mineral oil and petrolatum) are weighed, heated and mixed in a glass jar at 50° C. to 60° C. until visually uniform. Then the powders (silica, CMC, AVE/MA) are weighed and shake-blended together in a container. Thereafter, the powders are mixed into the non-aqueous carriers with a spatula until visually a uniform pink cream. D&C Red 28 (CAS 18472-87-2) or any other xanthene dye listed in Table 1 can be substituted into these formulas for the D&C Red 27.

Example II

A denture wearer places from 0.1 to 5 grams of any of the compositions described below on their denture. Then the subject inserts the denture into his/her mouth and presses it into place. After applying the composition, the composition prevents, reduces, inhibits, and/or kills microbes in the oral cavity or prevents, reduces, inhibits, calculus, tartar, plaque, and/or stain, in the oral cavity.

|  | A Grams | B Grams | C Grams | D Grams | E Grams | F Grams | G Grams |
|---|---|---|---|---|---|---|---|
| White Mineral Oil | 23.95 | 23.95 | 23.95 | 23.95 | 23.95 | 23.95 | 23.95 |
| Petrolatum, White | 21.909 | 21.809 | 19.909 | 18.9 | 15.81 | 18.91 | 9.91 |
| Carboxymethylcellulose Sodium | 24 | 24 | 24 | 24 | 24 | 24 | 24 |
| Silicon Dioxide, Colloidal | 1.14 | 1.14 | 1.14 | 1.14 | 1.14 | 1.14 | 1.14 |
| D&C Red 28 -CAS 18472-87-2 | 0.00001 | 0.0001 | 0.001 | 0.01 | 0.1 | 1 | 10 |
| Ca/Zn salt of AVE/MA or Mg/Zr salt of AVE/MA or Mg/Na/Zn salt of AVE/MA | 30 | 30 | 30 | 30 | 30 | 30 | 30 |
| AVE/MA (acid form) | 0 | 0.1 | 1 | 2 | 5 | 1 | 1 |

The colorant and non-aqueous carriers (mineral oil and petrolatum) are weighed, heated and mixed in a glass jar at 50° C. to 60° C. until visually uniform. Then the powders (silica, CMC, AVE/MA) are weighed and shake-blended together in a container. Thereafter, the powders are mixed into the non-aqueous carrier with a spatula until visually a uniform pink cream. D&C Red 27 or any other xanthene dye listed in the above Table 1 can be substituted into these formulas for the D&C Red 28.

Example III

The powdered portion of examples I and II are blended and swifted onto a pre-wet 20×40 sheet of polyester. The sheet is again sprayed with water and dried. The dried sheet is then mechanically softened and cut into denture shaped wafers. The denture wearer moistens the wafer under water and places it upon the denture. After applying the composition, the composition prevents, reduces, inhibits, and/or kills microbes in the oral cavity or prevents, reduces, inhibits, calculus, tartar, plaque, and/or stain, in the oral cavity.

What is claimed is:

1. A method of reducing or inhibiting calculus, tartar, plaque, or stain, in an oral cavity, by applying a denture adhesive composition to the oral cavity of a denture wearer in need thereof, the denture adhesive composition comprising:
    (a) from about 15% to about 70% by weight of the composition of a denture adhesive component;
    (b) from 0.001% to about 10% by weight of the composition of an antimicorbial colorant selected from the group consisting of Acid Yellow 73, Solvent Red 72, Acid Red 87, Pigment Red 90, Solvent Red 43, Acid Red 98, Acid Red 92, Solvent Red 48, Pigment Red 174, Acid Red 95, Solvent Red 73, Acid Red 51, Food Red 14, Pigment Red 172, Acid Red 94, Solvent Orange 16, Acid Red 52, Basic Violet, 4Acid Violet 9, Acid Red 50, Acid Red 289, Solvent Violet 10, Basic Red 1, Pigment ed 81, Basic Violet 10, Solvent Red 49, Pigment Violet 1, Basic Violet 11, Solvent Green 4, Mordant Red 27, lakes thereof, and mixtures thereof; and
    (c) a safe and effective amount of a non-aqueous denture adhesive carrier.

2. The method of claim 1 wherein the antimicrobial colorant is selected from the group consisting of Solvent Red 72, Acid Red 87, Pigment Red 90, Solvent Red 43, Acid Red 98, Acid Red 92, Solvent Red 48, Pigment Red 174, Acid Red 95, Solvent Red 73, Acid Red 51, Food Red 14, Pigment Red 172, Acid Red 94, Acid Red 52, Acid Red 50, Acid Red 289, Basic Red 1, Pigment Red 81, Solvent Red 49, lakes thereof, and mixtures thereof.

3. The method of claim 2 wherein the antimicrobial colorant is selected from the group consisting of Acid Red 87, Solvent Red 43, Acid Red 92, Solvent Rd 48, Solvent Red 73, Acid Red 51, Food Red 14, and mixtures thereof.

4. The method of claim 1 wherein the amount of antimicrobial colorant is from about 0.009% to about 2%, by weight of the composition.

5. The method of claim 4 wherein the amount of antimicrobial colorant is from about 0.05% to about 1%, by weight of the composition.

6. The method of claim 1 wherein the denture adhesive component is selected from the group consisting of natural gums, synthetic polymeric gums, AVE/MA, salts of AVE/MA, AVE/MA/B, salts of AVE/MA/IB, synthetic polymers, mucoadhesive polymers, water-soluble hydrophilic colloids or polymers having the property of swelling upon exposure to moisture to form a mucilaginous mass, hydroplilic polymers, saccharide derivatives, cellulose derivatives, karaya gum, guar gum, gelatin, algin, sodium alginate, tragacanth, chitosan, polyethylene glycol, acrylamide polymers, polyvinyl alcohol, polyamines, polyquarternary compounds, ethylene oxide polymers, polyvinylpyrrolidone, cationic polyacrylamide polymers, and mixtures thereof.

7. The method of claim 6 wherein the denture adhesive component is a salt of AVE/MA, or mixtures thereof, the salt containing a cation selected from the group consisting of Group IA and Group 2A cations of the periodic table, yttrium, titanium, zirconium, vanadium, chromium, manganese, iron, nickel, copper, zinc, boron, aluminum, sodium, and mixtures thereof.

8. The method of claim 7 wherein the cation is selected from the group consisting of strontium, zinc, iron, magnesium, calcium, sodium, and mixtures thereof, and wherein the amount of denture adhesive component is from about 20% to about 50%, by weight of the composition.

9. The method of claim 8 wherein the composition additionally comprises a cellulose derivative selected from the group consisting of hydroxyethylcellulose, hydroxypropylcellulose, hydroxypropylmethyl-cellulose, sodium carboxymethylcellulose, and mixtures thereof.

10. The method of claim 1 wherein the non-aqueous denture adhesive carrier is selected from the group consisting of a non-aqueous vehicle and a non-adhesive self supporting layer.

11. The method of claim 10 wherein the carrier is a non-aqueous vehicle is selected from the group consisting of liquid petrolatum, petrolatum, mineral oil, natural and synthetic oils, fats, natural and synthetic waxes, beeswax, lanolin, shellac, hydrocarbons, hydrocarbon derivatives, vegetable oil waxes, camauba, candelilla, bayberry wax, caprylic/capric triglycerides, corn oil, soybean oil, cottonseed oil, and mixtures thereof, in an amount of from about 20% to about 80%, by weight of the composition.

12. The method of claim 10 wherein the carrier is a non-adhesive self-supporting layer wherein the non-adhesive self-supporting layer is selected from the group consisting of polyester, polypropylene, nylon, rayon, cellulose acetate, non-adhesive cellulose derivatives, cloth, fibrous fleece, paper, plastic, leather, synthetic fibers, natural fibers, and mixtures thereof.

13. A method of providing an antimicrobial composition in an oral cavity effective for the treatment of plaque, by applying a denture adhesive composition to the oral cavity of a denture wearer in need thereof, the denture adhesive composition comprsing:
(a) from about 15% to about 70% by weight of the composition of a denture adhesive component;
(b) from 0.001% to about 10% by weight of the composition of an antimicrobial colorant selected from the group consisting of of Acid Yellow 73, Solvent Red 72, Acid Red 87, Pigment Red 90, Solvent Red 43, Acid Red 98, Acid Red 92, Solvent Red4 48, Pigment Red 174, Acid Red 95, Solvent Red 73, Acid Red 51, Food Red 14, Pigment Red 172, Acid Red 94, Solvent Orange 16, Acid Red 52, Basic Violet, Acid Violet 9, Acid Red 50, Acid Red 289, Solvent Violet 10, Basic Red 1, Pigment Red 81, Basic Violet 10, Solvent Red 49, Pigment Violet 1, Basic Violet 11, Solvent Green 4, Mordant Red 27, lakes thereof, and mixtures thereof: and
(c) a safe and effective amount of a non-aqueous denture adhesive carrier.

14. The method of claim 13 wherein the antimicrobial colorant is selected from the group consisting of Solvent Red 72, Acid Red 87, Pigment Red 90, Solvent Red 43, Acid Red 98, Acid Red 92, Solvent Red 48, Pigment Red 174, Acid Red 95, Solvent Red 73, Acid Red 51, Food Red 14, Pigment Red 172, Acid Red 94, Acid Red 52, Acid Red 50, Acid Red 289, Basic Red 1, Pigment Red 81, Solvent Red 49, lakes thereof, and mixtures thereof.

15. The method of claim 14 wherein the antimicrobial colorant is seleced from the group consisting of Acid Red 87, Solvent Red 43, Acid Red 92, Solvent Red 48, Solvent Red 73, Acid Red 51, Food Red 14, and mixtures thereof.

16. The method of claim 13 wherein the amount of antimicrobial colorant is from about 0.009% to about 2%, by weight of the composition.

17. The method of claim 16 wherein the amount of antimicrobial colorant from about 0.05% to about 1%, by weight of the composition.

18. The method of claim 13 wherein the denture adhesive component is selected from the group consisting of natural gums, synthetic polymeric gums, AVE/MA, salts of AVE/MA, AVE/MA/IB, salts of AVE/MA/IB, synthetic polymers, mucoadhesive polymers, water-soluble hydrophilic colloids or polymers having the property of swelling upon exposure to moisture to form a mucilaginous mass, hydrophillic polymers, saccharide derivatives, cellulose derivatives, karaya gum, guar gum, gelatin, algin, sodium alginate, tragacanth, chitosan, polyethylene glycol, acrylamide polymers, polyvinyl alcohol, polyamines, polyquarternary compounds, ethylene oxide polymers, polyvinylpyrrolidone, cationic polyacrylamide polymers, and mixtures thereof.

19. The method of claim 18 wherein the denture adhesive component is a salt of AVE/MA, or mixtures thereof, the salt containing a cation selected from the group consisting of Group IA and Group 2A cations of the periodic table, yttrium, titanium, zirconium, vanadium, chromium, marganese, iron, nickel, copper, zinc, boron, aluminum, sodium, and mixtures thereof.

20. The method of claim 19 wherein the cation is selected from the group consisting of strontium, zinc, iron, magnesium, calcium, sodium, and mixtures thereof, and wherein the amount of denture adhesive component is from about 20% to about 50%, by weight of the composition.

21. The method of claim 20 wherein the composition additionally comprises a cellulose derivative selected from the group consisting of hydroxyethylcellulose, hydroxypropylcellulose, hydroxypropylmethyl-cellulose sodium carboxymethylcellulose, and mixtures thereof.

22. The method of claim 13 wherein the non-aqueous denture adhesive carrier is selected from the group consisting of a non-aqueous vehicle and a non-adhesive self supporting layer.

23. The method of claim 22 wherein the carrier is a non-aqueous vehice is selected from the group consisting of liquid petrolacum, petrolatum, mineral oil, natural and synthetic oils, fats, natural and synthetic waxes, beeswax, lanolin, shellac, hydrocarbons hydrocarbon derivatives, vegetable oil waxes, carnauba, candelilla, bayberry wax, caprylic/capric triglycerides, corn oil, soybean oil, cottonseed oil, and mixtures thereof, in an amount of from about 20% to about 80%, by weight of the composition.

24. The method of claim 22 wherein the carrier is a non-adhesive self-supporting layer wherein the non-adhesive self-supporting layer is selected from the group consisting of polyester, polypropylene, nylon, rayon, cellulose acetate, non-adhsive cellulose derivatives, cloth, fibrous fleece, paper, plastic, leather, synthetic fibers, natural fibers, and mixtures thereof.

* * * * *